(12) United States Patent
Chen et al.

(10) Patent No.: US 7,297,838 B2
(45) Date of Patent: Nov. 20, 2007

(54) DOUBLED HAPLOID PRODUCTION AND GENETIC TRANSFORMATION

(75) Inventors: Yurong Chen, Manitoba (CA); Joseph Clifford Paul Dribnenki, Manitoba (CA)

(73) Assignee: Agrecore United

( * ) Notice: Subject to any disclaimer, the term of this patent is extended or adjusted under 35 U.S.C. 154(b) by 800 days.

(21) Appl. No.: 10/291,504

(22) Filed: Nov. 12, 2002

(65) Prior Publication Data

US 2003/0093829 A1  May 15, 2003

Related U.S. Application Data

(60) Provisional application No. 60/331,278, filed on Nov. 13, 2001.

(51) Int. Cl.
C12N 15/87   (2006.01)
C12N 15/82   (2006.01)
A01H 5/00    (2006.01)

(52) U.S. Cl. ........................ 800/294; 435/469

(58) Field of Classification Search ............ None
See application file for complete search history.

(56) References Cited

U.S. PATENT DOCUMENTS

| | | | | |
|---|---|---|---|---|
| 5,272,072 A | * | 12/1993 | Kaneko et al. ............. | 800/276 |
| 5,750,871 A | * | 5/1998 | Moloney et al. ............ | 800/294 |
| 5,994,624 A | * | 11/1999 | Trolinder et al. ........... | 800/278 |
| 6,140,553 A | * | 10/2000 | D'Halluin ................... | 800/278 |

OTHER PUBLICATIONS

Baillie et al 1992 Plant Cell Reports 11:234-237.*
Zhan et al 1988 Plant Molecular Biology 11:551-559.*
Bretagne-Sagnard et al 1996 Transgenic Research 5:131-137.*
Chen et al 1998 Plant Breeding 117:463-467.*
Ferrie, A.M.R., "Evaluation of *Brassica rapa* L. Genotypes for microspore culture response and identification of a highly embryogenic line.", *Plant cell reports*; (1995), vol. 14, p. 580-584.
Baillie, A.M.R., "In vitro culture of isolated microspores and regeneration of plants in *Brassica campestris*.", *Plant cell reports*; (1992), vol. 11, p. 234-237.
Chen, Y., "High frequency of plant regeneration from anther culter in flax, *Linum usitatissimum* L." *Plant breeding*; vol. 117, (1998), p. 463-467.
Dunwell, J.M., "Role of sucrose in microspore embryo production in *Brassica napus* ssp. Oleifera." *Journal of experimental botany*; vol. No. 170, Sep. (1985), p. 1478-1491.
Guo, Y.D., "Isolated microspore culture and plant regeneration in rye (*Secale cereale* L.)." *Plant cell reports*; (2000), vol. 19, p. 875-880.
Kuchuk, N., "Plant regeneration from leaf protoplasts of evening primrose (*Oenothera hookeri*)." *Plant cell reports*; (1998) vol. 17 p. 601-604.

* cited by examiner

*Primary Examiner*—Phuong Bui
*Assistant Examiner*—Brent T Page
(74) *Attorney, Agent, or Firm*—Michael R. Williams; Ryan W. Dupuis; Adrian D Battison

(57) ABSTRACT

Development of an efficient and cost-effective doubled haploid production system and genetic transformation system are the prerequisite to initiate haploid breeding and genetic modification in flax respectively. Pre-culturing anthers on a high osmotic, high auxin and high mineral salt concentration for a period of time before transfer to a low osmotic, low auxin and low salt concentration significantly increased the overall efficiency of regeneration or anther efficiency than directly culturing anthers on a low osmotic, low auxin and low salt concentration medium. This culture procedure also dramatically reduced the frequency of shoot regeneration from somatic cells in anther culture. Using this procedure, a highly efficient anther culture-derived callus based transformation system was developed. The transformation efficiency of anther culture-derived callus based transformation system was four times higher than the best reported transformation efficiency using hypocotyls as the ex-plants in *Agrobacterium tumefaciens* based transformation system or particle bombardment based transformation system. The frequency of escape in anther culture-derived callus based transformation system was one third of that in hypocotyl-based transformation system using *A. tumefaciens* or one half using particle bombardment. This very high efficient transformation system will prove to be very valuable in basic research for gene discovery and practical applications in genetic engineering for improved traits.

3 Claims, No Drawings

DOUBLED HAPLOID PRODUCTION AND GENETIC TRANSFORMATION

This application claims priority under 35 USC § 119(e) to Provisional Patent Application Ser. No. 60/331,278 filed on Nov. 13, 2001.

BACKGROUND OF THE INVENTION

Development of an efficient and cost-effective doubled haploid production system in flax (*Linum usitatissimum* L.) is a prerequisite for applying doubled haploid technology to practical breeding purposes. Successful regeneration of haploid/doubled haploid plants through anther culture has been previously achieved in fiber flax and oil flax (Sun and Fu, 1981, *Acta Genet Sin* 8:369-374; Nichterlein et al., 1991, *Euphytica* 58:157-164). However, the overall efficiency of regeneration from anther culture was very low and the frequency of regeneration from the somatic tissue-derived plants was quite high (Friedt et al., 1995, *Plant Breed* 114: 322-326). Consequently, the efficiency of doubled haploid production was too low for any meaningful practical applications or even basic research purposes. The overall efficiency of regeneration from anther culture in flax has subsequently been improved but in these experiments the frequency of regeneration from somatic tissues remained high (Chen et al., 1998, *Euphytica* 102: 183-189; Chen et al., 1998, *Plant Breed* 117: 463-467; Chen et al., 1998, *Plant Cell Reports* 18:44-48). As will be apparent to one knowledgeable in the art, the progeny are therefore not all doubled haploids and must be screened for some applications. For success, it is necessary to increase the overall efficiency of regeneration, to decrease the frequency of regeneration from somatic tissues and to increase the overall efficiency of doubled haploid production.

U.S. Pat. No. 5,929,300 teaches a pollen-based transformation method wherein pollen is germinated and transformed with *Agrobacterium*. The treated pollen can then be used to pollinate a receptive plant. It is of note that this patent also remarks that "the cells of some plant species are not easily maintained in tissue culture and are not easily regenerated into somatic clones" (column 1, lines 31-33).

Furthermore, Dunwell and Thurling (Dunwell and Thurling, 1985, *J Exp Botany* 36: 1478-1491) taught that "substantially better microspore viability is achieved if anthers of both spring and winter cultivars of rape are cultured on sucrose concentrations of 16-20% rather than the more usually recommended 8-10%. These high concentrations allow embryo induction in a larger number of anthers and reduce the inter-cultivar variations in response." Furthermore, it was noted that anthers maintained on these high concentrations did not produce macroscopic embryos and it was recommended that transfer to lower sucrose concentrations take place during the culture phase to take full advantage of the initial high survival values. However, they also noted that "perhaps the problem of secondary embryogenesis which is so frequently found amongst microspore-derived embryos of *Brassica* species may be caused by trauma of an approximate ten fold reduction in osmotic pressure". Thus, the paper concludes that subsequent growth on low sucrose may not be desirable. In addition, two other papers describe the advantages of transferring microspores from high sucrose concentration to lower sucrose concentration for embryo induction in *Brassica* (Baillie et al. 1992 *Plant Cell Reports* 11:234-237; Ferrie et al. 1995 Plant Cell Reports 14:580-584). However, it is important to note that none of these papers discuss the effect of the transfer from high sucrose to low sucrose on plant regeneration (hapoid or doubled haploid plants) or the application of the protocol for transformation purposes. It is also of note that reduction of regeneration from somatic tissue was not discussed or disclosed.

Chen et al. (Chen et al., 1998, *Plant Breeding* 117: 463-467) teaches a high frequency method of plant regeneration from anther culture in flax by optimizing induction media composition. Therein, it is noted that "preliminary results . . . showed that culture of anthers on a medium containing 15% sucrose for a certain period of time and then transfer of anthers to a medium containing a lower sucrose concentration dramatically increased the overall efficiency of regeneration." It is important to note that the necessary period of time and the lower sucrose concentration are not specifically disclosed.

The establishment of an efficient plant regeneration method is a prerequisite for the development of efficient transformation protocols using tissue culture. Somatic diploid tissues, e.g. hypocotyl segments or cotyledons have been used as the ex-plants to regenerate fertile transgenic flax plants through *Agrobacterium* mediated or particle bombardment-based approaches (Basiran et al. 1987, *Plant Cell Reports* 6:396-399; Zhan et al., 1988, *Plant Molecular Biology* 11:551-559; Wijayanto and McHughen, 1999, *In Vitro Cell Dev Biol-Plant* 35:456-465). However, the transformation efficiency using hypocotyl segments as ex-plants was quite low and the escape frequency was very high (Dong and McHughen, 1993, *Plant Sci.* 88:61-71; Wijayanto and McHughen 1999). As will be apparent to one knowledgeable in the art, protocols which increase transformation efficiency, reduce the frequency of escape and allow the regeneration of homozygous transgene lines in the T0 generation would facilitate the use of genetic transformation to improve the agronomic and quality traits of flax in order to better meet market needs. In addition, the development of a high throughput transformation protocol would facilitate the use of flax as a model species for gene discovery and functional genomics as flax has the smallest genome size of any major field crop.

Microspores and microspore-derived haploid cells (embryos/calluses) are ideal targets for genetic transformation since transgenes can be immediately fixed upon spontaneous chromosome doubling or colchicine treatment. The immediate homozygosity of transgenes in microspore-derived transgenic plants greatly simplifies the procedure for genetic analysis and isolation of homozygous transgenic lines for further applications. Successful recovery of transgenic plants through microinjection, particle bombardment, or silicon carbide whisker treatment of microspores/microspore-derived embryo/callus has been reported in a few species (Brisibe et al., 2000, *J Exp Botany* 51: 187-196; Neuhas et al, 1987, *Theor Appl Genet* 75: 30-36; Jahne et al. 1994, *Theor Appl Genet* 89:525-533; Stöger et al. 1995, *Plant Cell Rep* 14:273-278; Fukuoka et al. 1998, *Plant Cell Rep* 17:323-328). *Agrobacterium* mediated transformation of microspore/microspore-derived embryo has been reported in *Brassica napus*, Datura and Nicotiana (Sangwan et al., 1993, *Plant Sci* 95: 99-115; Swanson and Erickson 1989, *Theor Appl Genet* 78:831-835; Pechan 1989, *Plant Cell Rep* 8:387-390; Huang 1992, *In Vitro Cell Dev Biol* 28P:53-58). However, as discussed above, these authors did not present detailed data and the transformation efficiency was very low in these studies. Microspore-derived embryos should have similar regeneration capacity as immature zygotic embryos. One of the main advantages of microspore-derived embryos as the ex-plants for genetic transformation is the immediate isolation of homozygous transgene lines. But the advantage of using microspore-derived embryos may not be easily realized in species where a high frequency microspore embryogenesis system is not available or access to immature zygotic embryos is very convenient, such as barley, wheat, corn and rice. It is also true to species where access to other highly regenerable plant tissues such as cotyledons or hypocotyls is very convenient, such as Brassica. This explains why there are a few preliminary reports in canola using microspore-derived embryos as the ex-plants for genetic transformation and no reports of using anther culture-derived callus as the ex-plants for genetic transformation. In flax and species that do not have other highly regenerable tissues, anther culture-derived callus/embryos would be the best choice as the ex-plants for transformation.

SUMMARY OF THE INVENTION

According to a first aspect of the invention, there is provided a method of regenerating plants comprising:
  providing callus from a plant;
  growing the callus on a high osmotic induction media for a period of time;
  transferring the callus to a low osmotic induction media;
  growing the callus on a regeneration media, said regeneration media for regenerating shoots; and
  growing the callus on an elongation media for elongating the shoots.

According to a second aspect of the invention, there is provided a method of transforming and regenerating plants comprising:
  providing callus from a plant;
  growing the callus on a high osmotic induction media for a period of time;
  transferring the callus to a low osmotic induction media;
  transforming the callus with a nucleic acid molecule while growing the callus in the low osmotic induction media;
  growing the callus on a regeneration media, said regeneration media for regenerating shoots; and
  growing the callus on an elongation media for elongating the shoots.

According to a third aspect of the invention, there is provided a method of transforming and regenerating plants comprising:
  removing anthers from a bud of a plant;
  preparing anther culture from the anthers;
  growing the anther culture into a callus;
  transforming the callus with a nucleic acid molecule;
  growing the callus on a regeneration media, said regeneration media for regenerating shoots; and
  growing the callus on an elongation media for elongating the shoots.

According to a fourth aspect of the invention, there is provided a method of transforming and regenerating plants comprising:
  providing tissue from a plant;
  growing the tissue on a high osmotic induction media for a period of time;
  transferring the tissue to a low osmotic induction media;
  transforming the tissue with a nucleic acid molecule while growing the callus in the low osmotic induction media;
  growing the tissue on a regeneration media, said regeneration media for regenerating shoots; and
  growing the tissue on an elongation media for elongating the shoots.

According to a fifth aspect of the invention, there is provided a plant, plant tissue or plant cell regenerated according to the method described above.

According to a sixth aspect of the invention, there is provided a plant, plant tissue or plant cell including a transgene wherein said transgene has been introduced according to one of the above-described methods.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

DEFINITIONS

As used herein, "doubled haploid" refers to a plant or tissue portion generated from a haploid cell.

As used herein, "anther" refers to the pollen-bearing portion of a stamen.

As used herein, "somatic tissue" refers to diploid tissue.

As used herein, "callus" refers to undifferentiated tissue.

As used herein, "cotyledon" refers to a seed leaf.

As used herein, "transformation" and "transformed" refer to the introduction of nucleic acid elements into cells.

As used herein, "osmotic regulator" refers to compounds which affect osmotic pressure of a cell.

Described herein is an efficient method of producing doubled haploid plants which has high regeneration efficiency and doubled haploid production and also has a low frequency of regeneration from somatic tissues. The method involves providing callus from a plant and growing the callus on a high osmotic induction media for a period of time, then transferring the callus to a low osmotic induction media. This significantly increased the overall efficiency of regeneration compared to culturing anthers directly onto a low osmotic induction media. Furthermore, the percentage of somatic cell-derived plants was also greatly reduced, as discussed below. The callus is then grown on a regeneration media for regenerating shoots; and then grown on an elongation media for elongating the shoots. As will be apparent to one skilled in the art, the callus may be for example anther-derived or microspore-derived callus/embryo.

In some embodiments, the callus is transformed with a nucleic acid molecule while grown on the low osmotic induction medium. As will be apparent to one knowledgeable in the art, any suitable transformation method, for example, *Agrobacterium*-mediated transformation, electroporation or particle bombardment, may be used. The nucleic acid molecule may be, for example, any suitable or desirable element, for example, a resistance gene, a metabolic gene or the like.

As described below, the transfer from high sucrose to low sucrose significantly increased plant regeneration frequency rather than callus/embryo induction efficiency as taught in the prior art. Transfer from high salt concentration to low salt concentration also significantly increased plant regeneration frequency not callus/embryo induction efficiency. In addition, the transfer from high sucrose to low sucrose dramatically reduces the regeneration from somatic tissue, which significantly reduces the cost associated with material handling in routine doubled haploid production system, as described below.

In another embodiment, there is described a method of transforming anther-derived calluses using methods described below. In one embodiment, the transformation is carried out by co-cultivating 2-7 week old or 4-6 week old sliced calluses with *Agrobacterium*.

It is of note that most crop species do not have highly efficient haploid/doubled haploid regeneration systems through anther/microspore culture. In barley and some *Brassica* species where anther/microspore have been used for haploid/doubled haploid plant regeneration, plants are regenerated through embryogenesis, i.e. through microspore-derived embryos. Attempts have been made to use microspore-derived embryos as ex-plants for *Agrobacterium* based transformation in *Brassica* (Swanson and Erickson 1989 Theor Appl Genet 78:831-835; Pechan 1989 Plant Cell Reports 8:387-390; Huang 1992 In Vitro Cell. Dev. Biol. 28P:53-58). However, as discussed above, no results have been published using anther culture/microspore culture derived callus as the ex-plants for transformation probably due to the development of embryogenesis protocol or low plant regeneration efficiency from anther/microspore culture in other species.

The high osmotic induction media may be, for example, but by no means limited to, 15-24% sucrose, 18-24% sucrose, 15-24% maltose, 6-9% sucrose+6-9% PEG, 6-15% PEG, 2×-4× salts. As will be appreciated by one knowledgeable in the art, other suitable osmotic regulators may also be used at suitable concentrations.

The low osmotic induction media may be, for example, ½-¼ salts or 1-6% sucrose. As will be appreciated by one knowledgeable in the art, other suitable osmotic regulators may also be used at suitable concentrations.

The callus may be grown on the high osmotic induction media for 1-21 days, or for 1-14 days, or for 2-14 days or for 2-7 days.

As described below, for sucrose, it has been demonstrated that pre-culturing anthers on 18% sucrose medium for 7 days before transfer to ¼ A22C medium had a significantly higher overall efficiency of regeneration than pre-culturing anthers on a 15% sucrose medium. The overall efficiency of regeneration was reduced when anthers were pre-cultured on 24% sucrose medium for 7 days before transfer to ¼ A22C medium as compared pre-culturing on 15% sucrose medium. However, the overall efficiency of regeneration may be increased if the culture duration on 24% sucrose medium is reduced. For PEG, pre-culturing anthers on 9% PEG+6% sucrose or 12% PEG+3% sucrose resulted in the similar overall efficiency of regeneration as pre-culturing anthers on 15% sucrose medium for 7 days. While the overall efficiency of regeneration was reduced when anthers were pre-cultured on 15% PEG for 7 days, the overall efficiency of regeneration may be increased if the duration of pre-culturing anthers on 15% PEG medium is reduced. It is also of note that comparable results were obtained for sucrose and maltose when anthers were cultured at 6, 9 and 15% sucrose or maltose medium. For lactose, similar results were obtained when anthers were cultured on 9% sucrose or lactose depending on the specific genotype. For salt concentration, the overall efficiency of regeneration was reduced when the anthers were cultured on 2× salts medium for 28 days as compared to 1× salts medium. Culturing anthers on 4× salts medium for 28 days completely inhibited callus induction. For the second step of callus induction, similar results were obtained for medium containing 6% or 1% sucrose. For the salt concentration, the lowest concentration tested was ¼ salts medium that increased the overall efficiency of regeneration. For the duration of pre-culture, current 7 days' pre-culture was chosen for the regeneration efficiency and for the convenience of operation. It is of note that a longer period of time may be required for a lower osmotic medium and shorter period of time may be required for a higher osmotic medium.

It is of note that the high osmotic pre-culture and low osmotic callus induction scheme will likely work in any species, particularly in which regeneration from somatic tissue is a major problem in anther/microspore culture (e.g. sunflower, Coumans and Zhong 1995 Plant Cell Tissue and Organ Culture 41:203-209). For genetic transformation, the high osmotic pre-culture and low osmotic callus induction scheme will likely work in any species where anther culture-derived callus or callus from any source can be used as an ex-plant for transformation. Thus, in another embodiment of the invention, there is provided a method of producing a transgenic plant comprising providing a callus, growing the callus on high osmotic media, transferring the callus to low osmotic media and transforming the callus with a transgene.

Furthermore, since anther culture-derived callus consists of microspore-derived callus and somatic tissue-derived callus, it is likely that microspore-derived callus or somatic tissue-derived callus can also be transformed using the above-described protocols. It is also likely that other diploid tissue, for example, hypocotyl, embryo, immature zygotic embryo or cotyledon-derived callus can also be used as an ex-plant using the above-described methods. Thus, in another embodiment, the invention is directed to the transformation of callus, embryo, hypocotyl, cotyledon, immature zygotic embryo and other diploid tissues using the above-described methods.

The invention will now be explained by way of examples. However, the invention is not limited to the examples.

1. Doubled Haploid Production

EXAMPLE I

Plant materials

A number of flax genotypes, including recently registered varieties, $F_1$ hybrids, and breeding populations at different developmental stages of the variety development process were used as donor plants. As discussed above, however, any suitable flax variety as well as any other suitable plant may be used. Seeds of donor genotypes were germinated and grown in a growth chamber at 14/8° C. (day/night) with a 16 h-photo-period and a 75% relative humidity. The light density measured at the top of the pots was approximately 300 $\mu molm^{-2}s^{-1}$ photosynthetic photon flux density (PPFD) supplied by a mixture of fluorescent tubes and incandescent bulbs. All plants were grown in steam-sterilized mixture of soil, peat moss, vermiculite and sand in 3:2:1:2 ratio (in volume) in 16.5 cm diameter pots. The plants were watered and fertilized with diluted 20-20-20 ($N:P_2O_5:K_2O$) (Plant Products Company Ltd., Brampton, ON) at the rate of 4 g/L as required.

EXAMPLE II

Anther culture

Buds were collected when the microspores were at mid uni-nucleate stage previously determined by microscopic observation of anthers stained with 1% aceto-carmine. Harvested buds were surface sterilized first in 70% ethanol for 1 min, then in 2% sodium hypochlorite (38% commercial Javex) for 10 min and finally rinsed three times with sterile distilled water. Five anthers from each of two buds (total 10) were removed under a dissecting microscope and inoculated onto an induction medium.

Different induction media and callus induction procedures were used for each experiment. The induction medium was solidified with 0.4% Sea Plaque agarose (FMC Bioproducts, Rockland, Me.). The macro and micro salts and agarose were all autoclaved at 121° C. for 15 min whereas the other components of the medium were filter sterilized (Nalgene 0.2 μm cellulose acetate filter, Sybron, Rochester, N.Y.). Three ml of medium was poured into sterile plastic petri dishes (35×10 mm Felcon no. 3001, Bectin Dickinson, Oxnard, Calif.). The three small petri dishes containing 10 anthers each were placed in a large (100×15 mm) plastic petri dish (Fisher Scientific, Nepean, ON) with several drops of sterile water to maintain humidity. The large petri dishes were wrapped with parafilm and incubated at 35° C. for 1 day and then at 25° C. for an additional 27 days in the dark. The induced calluses were then transferred to the regeneration medium.

The regeneration medium was the modified $N_6$ medium (Nichterlein et al., 1991, Chen et al., 1998) contained 375 mg/L glutamin, 250 mg/L asparagine, 125 mg/L serine, 30 g/L sucrose, 1 mg/L zeatin and 4 g/L phytagel. Twenty-five ml of medium was dispensed into sterile plastic petri dish (100×25 mm) (Phoenix Biomedical Missisauga, ON). Regeneration was conducted at constant 25° C. with a 16 h photo-period, light density of 40 $\mu molm^{-2}s^{-1}$ PPFD supplied by fluorescent tubes and a 75% relative humidity. Calluses with shoots regenerated were transferred to a shoot elongation medium. Elongated shoots were cut and transferred to a rooting medium.

Elongation medium was liquid MS (Murashige and Skoog, 1962, *Physiol Plant* 15:473-479) medium basal containing 10 g/L sucrose and 0.2 mg/L indole-acetic acid (IAA). The rooting medium was the half strength of MS medium containing 10 g/L sucrose, 1 mg/L indole-butyric acid (IBA), 0.5 mg/L α-naphthalene-acidic acid (NAA), 2.5 g/L activated charcoal and 7 g/L agar. Shoot elongation and shoot rooting were conducted in test tubes (25×100 mm, Sigmaware™, Sigma, St. Louis, Mo.). All components of the elongation medium and rooting medium were autoclaved at 121° C. for 15 min. Cultures were incubated at the same condition as for shoot regeneration. Rooted plants were transferred to the soil and maintained in a mist chamber for about one week and subsequently transferred to a growth chamber for further development. The percentage of anthers producing calluses was calculated as the number of anthers producing calluses per 100 inoculated anthers. The overall efficiency of regeneration was defined as the number of calluses forming shoots per 100 inoculated anthers. The anther efficiency was computed as the number of anthers producing shoots/per 100 inoculated anthers. The frequency of microspore-derived plants was determined using polymerase chain reaction based molecular marker analysis (Chen et al., 1998, Plant Cell Reports 18: 44-48; Chen et al., 2001, *Plant Breed* 120:82-84). Fertile microspore-derived plants were considered as true doubled haploid plants.

EXAPMLE III

Pre-Culture of Anthers on a High Sucrose Medium

Genotypes an Agricore United™ proprietary flax line, 96-3, 96-45 and 98-200 were used to study the effect of pre-culturing anthers on a high sucrose medium for a period of time before transfer to a low sucrose medium. Anthers were pre-cultured on $A_{22}C$ medium (Chen et al., 1998) containing 15% sucrose for 0 day (6% CK), 2 day, 7 day, 14 day and 28 days (15% CK) before transfer to the same $A_{22}$-C medium containing 6% sucrose. The total callus induction period was 28 days. The induced callused were transferred to the modified N6 regeneration medium for shoots regeneration.

EXAMPLE IV

Effect of Polyethylene Glycol (PEG) on Callus Induction and Shoot Regeneration

Genotype 98-200 was used to investigate the effect of PEG concentration on callus induction and shoot regeneration. Anthers pre-cultured on $A_{22}$-C medium containing 15% sucrose ($A_{22}$-C-15) for 7 days before transfer to the medium containing 6% sucrose for a total of 28 days were considered as control. For other treatments, anthers were pre-cultured on the same medium containing 9% PEG+6% sucrose (PEG-9), 12% PEG+3% sucrose (PEG-12) or 15% PEG+0% sucrose (PEG-15) respectively for the same period of time as the control before transfer to the $A_{22}$-C containing 6% sucrose for a total of 28 days. Induced calluses were transferred to the modified N6 regeneration medium for shoot regeneration.

EXAMPLE V

Pre-Culture of Anthers on a High Salt Medium

Genotypes 99-182, 99-183, 98-87 and 98-88 were used to investigate the effect of pre-culturing anthers on a high salt concentration medium for a period of time before transfer to a low salt concentration medium. Anthers were inoculated on a medium containing full strength $A_{22}C$ mineral salts, 8 mg/L 2,4-D, 1 mg/L BAP and 15% sucrose for one week. Anthers were subsequently transferred to a medium containing ¼ strength $A_{22}C$ mineral salt medium, 2 mg/L 2,4-D, 1 mg/L BAP and 6% sucrose for another three weeks for callus induction. As a control, anthers were inoculated on a medium containing full strength $A_{22}C$ mineral salts, 8 mg/L 2,4-D, 1 mg/L BAP and 15% sucrose for one week. Anthers were then transferred to the medium containing full strength $A_{22}C$ mineral salt, 2 mg/L 2,4-D, 1 mg/L BAP and 6% sucrose for an additional three weeks. Therefore, the difference between the treatment and control was the mineral salt concentration in the second step of the callus induction process. The total induction period was 28 days. The induced callused were transferred to the modified $N_6$ regeneration medium for shoot regeneration.

EXAMPLE VI

Effect of Sucrose Concentration During Pre-Culture

Genotype 99-186 was used to exam the effect of sucrose concentration during pre-culture on callus induction and shoot regeneration. The control medium contained the full strength of A22 salts, vitamins, amino acids, 8 mg/l 2,4-D, 1 mg/l BAP, 15% sucrose (A15-D). The other media contained 18%, 21% or 24% sucrose. Anthers were cultured on these media for one week before transfer to ¼ A22C medium that contained ¼ strength of A22 salts, full strength of vitamins, amino acids, 2 mg/l 2,4-D, 1 mg/l BAP, 6% sucrose for additional three weeks. Induced calluses were transferred to the modified $N_6$ medium for shoot regeneration.

EXAMPLE VII

Effect of Sucrose Concentration at the Second Step of Callus Induction

Genotype 99-187 was used to test the effect of sucrose concentration at the second step of callus induction on callus induction and shoot regeneration. Anthers were pre-cultured on medium containing the full strength of A22 salts, vitamins, amino acids, 8 mg/l 2,4-D, 1 mg/l BAP, 15% sucrose (A15-D) for one week. They were subsequently transferred 4 types of media containing ¼ strength of A22 salts, full strength of vitamins, amino acids, 2 mg/l 2,4-D, 1 mg/l BAP, supplemented with different concentration of sucrose (6%, 3%, 1% and 0%) for additional three weeks. Induced calluses were transferred to the modified $N_6$ medium for shoot regeneration.

2. Genetic Transformatom

EXAMPLE VIII

Plant Materials

An Agricore United proprietary flax line was used as the donor materials. Plant growth conditions were the same as for doubled haploid production.

EXAMPLE IX

Callus Induction and Procedures

Anther culture medium and culture procedures were the same as the experiment to determine the effect of pre-culturing anthers on high salt medium. Anthers were inoculated on a medium containing full strength $A_{22}C$ mineral salts, vitamins, 750 mg/L glutamin, 8 mg/L 2,4-D, 1 mg/L BAP, 15% sucrose and 4 g/L agarose. They were cultured at 35° C. for one day before transfer to 25° C. for additional six days. Anthers were subsequently transferred to a medium containing ¼ strength $A_{22}C$ mineral salts, full strength of vitamins, 750 mg/L glutamin, 2 mg/L 2,4-D, 1 mg/L BAP, 6% sucrose and 4 g/L agarose. They were cultured at 25° C. for an additional one to six weeks at 25° C. in the dark for callus induction.

EXAMPLE X

*Agrobacterium* Preparation

The vector DNA containing the gusA and hph genes (Wang et al., 1997, *J Genet Breeding* 51: 325-334) was introduced into *Agrobacterium tumefaciens* strain AGL1 by electroporation. The gusA encoding for beta-glucuronidase (GUS) driven by a ubiquitin promoter was used as a reporter gene in histochemical assay, and intron-disrupted hph encoding for hygromycin phospho-transferase under control of CaMV 35S promoter was used as selectable marker to select transformed cells. Bacteria culture was prepared by inoculating 50 mL liquid LB medium (1% tryptone, 0.5% yeast extract and 0.5% sodium chloride) containing 50 mg/L spectinomycin and 20 mg/L rifampicin with a 2 mL of 48 hrs bacterial culture in LB medium. The 2 mL culture was inoculated with a single colony from a freshly streaked LB plate (LB medium supplemented with 1.2% agar) containing 50 mg/mL spectinomycin and 20 mg/mL rifampicin. The pH of LB medium was adjusted to 7.0 before autoclaving. The 50 mL bacterial culture was incubated at 26° C. overnight with vigorous agitation. The bacterial culture was centrifuged at 3000 rpm for 20 minutes and the pellet was re-suspended in liquid MS medium containing 3% glucose. The step was repeated twice and the pellet was re-suspended in 50 mL liquid MS medium containing 3% glucose for inoculation.

EXAMPLE XI

Co-cultivation and Callus Induction and Plant Regeneration

Anther culture-derived calluses were cut while in an *Agrobacterium* suspension using forceps. Sliced calluses were filtered through a filter paper and placed on a co-cultivation medium for approximately six days. The co-cultivation medium was the same as the medium for the second step of callus induction in anther culture, i.e, ¼ $A_{22}$ C medium. Calluses following co-cultivation were washed in liquid MS medium containing 3% sucrose and placed on a selection/callus re-induction medium for two weeks. The selection/callus re-induction medium was the co-cultivation medium supplemented with 5 mg/L hygromycin and 250 mg/L timentin. Re-induced calluses were transferred to a selection/shoot regeneration medium and cultured at 25° C. under light and sub-cultured once every two weeks. The selection/shoot regeneration medium was the same medium as for shoot regeneration in anther culture supplemented with 5 mg/L hygromycin and 250 mg/L timentin. Regenerated shoots were transferred to an elongation medium. The elongation medium was the same as for anther culture supplemented with 10 mg/L hygromycin and 250 mg/L timentin for several days. A basal stem segment of each shoot was excised for histo-chemical GUS assay. Shoots from GUS-positive segments were rooted in a rooting medium. The rooting medium was similar to the shoot elongation medium. However, 7 g/L agar was added and timentin was reduced to the concentration of 150 mg/L. Plant-lets with well-developed roots were transplanted into soil in pots and kept in a mist-chamber for several days before moved to a growth chamber. The selected plants were allowed to mature and sterile plants were treated with colchicine to double chromosomes. Seeds harvested from fertile plants were germinated and the segregation pattern of the transgenes was analyzed.

EXAMPLE XII

GUS Staining Procedures

Calluses from co-cultivation and selection/callus re-induction stage, and shoot stem from the regenerated shoots after selection were sampled to determine transient and stable GUS gene expression. Plant materials were immersed in 100 μL of X-Gluc (5-bromo-4-chloro-3-indodyl-beta-delta-glucuronic acid) solution consisting of 100 mM sodium phosphate (pH 7.0), 0.5 mM potassium ferro-cyanide, 0.5 mM potassium ferri-cyanide, 10 mM ethylene diamine tetraacetic acid (EDTA) and 0.15% X-Gluc in an eppendorf tube. The eppendorf tubes were incubated at 37° C. overnight. The tissues were de-stained in 95% ethanol for a few hours if necessary. Transformation status of callus or shoot was determined according to the presence or absence of blue spots in the tissues.

EXAMPLE XIII

Results

As discussed above, pre-culture of anthers on 15% sucrose medium for 2 to 7 days before transfer to a 6% sucrose medium significantly increased the overall efficiency of regeneration or the anther efficiency as compared to culturing anthers directly on a 6% sucrose medium for 28 days. As can be seen in Table 1, the results were consistent for all four genotypes investigated, indicating that 2 to 7 days was preferable, although up to 14 days still showed desirable results. Furthermore, this culture procedure dramatically increased the percentage of microspore-derived plants and reduced the percentage of somatic cell-derived plants as compared to control (Table 2).

Pre-culture of anthers on media containing 9% PEG in combination with 6% sucrose (PEG-9) or 12% PEG in combination with 3% sucrose (PEG-12) had similar overall efficiency of regeneration or anther efficiency as pre-culture of anthers on 15% sucrose ($A_{22}$-C-15) for 7 days. This may indicate that most of the 15% sucrose acts as an osmotic regular and that the function of sucrose as an osmoticum can be replaced by non-metabolizable osmoticum, such as polyethylene glycol (Table 3).

Pre-culture of anthers on a full strength of $A_{22}$-C medium for 7 days before transfer to ¼ strength of $A_{22}$-C did not affect the percentage of anthers producing calluses. However, this culture procedure significantly increased the overall efficiency of regeneration or the anther efficiency for three of four genotypes tested as compared to culturing anthers directly on a full strength of $A_{22}$-C for 28 days (Table 4).

Increase of sucrose concentration from 15% to 18% during pre-culture significantly increased callus induction and shoot regeneration. Further increase in sucrose concentration decreased callus induction and shoot regeneration. However, there was no significant difference between media containing 15% sucrose and 21% sucrose. The percentage of anthers producing calluses, overall efficiency of regeneration and anther efficiency was significantly reduced in medium containing 24% sucrose in comparison with the medium containing 15% sucrose (Table 5).

Media containing different levels of sucrose at the second step of callus induction had significantly higher percentage of anthers producing calluses, overall efficiency of regeneration and anther efficiency than medium without any sucrose. However, there were no significant differences between media containing 10, 30 or 60 g/l sucrose in terms of the percentage of anthers producing calluses, overall efficiency of regeneration and anther efficiency (Table 6).

For Agrobacterium mediated transformation of microspore-derived callus, the duration of callus induction selection had a dramatic effect on shoot regeneration and transformation (Table 7). Specifically, a long period of selection apparently inhibited shoot regeneration from transformed callus and decreased transformation. Thus, a two-week selection regime had a higher efficiency of shoot regeneration and transformation than a four-week selection regime.

Furthermore, Agrobacterium concentration had a significant impact on shoot regeneration and genetic transformation (Table 8). High Agrobacterium concentration appeared to inhibit shoot regeneration from the transformed cells and subsequently reduce the efficiency of transformation. That is, efficiency of shoot regeneration and transformation was higher with low Agrobacterium concentration (OD=0.3) than with high Agrobacterium concentration (OD=1.2).

The age of the ex-plants for co-cultivation also had an impact on regeneration and transformation (Table 9). Specifically, five-week old microspore-derived callus had a significantly higher regeneration and transformation efficiency than seven-week old callus. This could mostly be due to the reduced regeneration capacity of old callus or less efficient interaction between old callus and Agrobacterium.

Of 48 plants grown to maturity, 32 plants (66.7%) were fertile. These fertile plants could be derived from doubled haploid cells before integration of a transgene and doubled haploid cells after the integration of the transgene or from somatic tissue. The remaining 16 (33.3%) sterile plants were likely transformed haploid plants without spontaneous chromosome doubling since the percentage of the sterile haploid plants is similar to that in our routine doubled haploid production system. The chromosomes of sterile haploid plants could be easily doubled by treatment with colchicine. Therefore, transgenes in colchicine-doubled plants would be homozygous. Genetic analysis of 24 plants that produced enough seeds for progeny analysis showed that approximately 8.3% (2 of 24) of them had homozygous transgenes. Approximately 70.8% (17 of 24) of them had a single transgene integration whereas 12.5% (3 of 24) had a two loci integration, as shown in Table 10. The segregation pattern of the remaining two plants indicated that they were chimeras.

EXAMPLE XIV

Discussion

Callus induction and shoot regeneration in anther culture of flax has been improved significantly by modifying medium components in the induction medium. However, the frequency of regeneration from somatic tissues using the improved induction medium containing 6% sucrose remained high (Chen et al., 1998c). The frequency of regeneration from somatic tissues could be reduced when anthers were cultured in the same induction medium containing 15% sucrose. However, the overall efficiency of regeneration was significantly reduced in 15% sucrose medium. The overall efficiency of doubled haploid production was similar between 6% sucrose and 15% sucrose medium (Chen et al. 1998). In this study, pre-culture of anthers on a 15% sucrose medium for 7 days before transfer to a 6% sucrose medium significantly increased the overall efficiency of regeneration or anther efficiency. This culture procedure also dramatically reduced the frequency of regeneration from the somatic tissues of anthers. Consequently, the overall efficiency of doubled haploid production was significantly improved. Furthermore, the beneficial effect of this culture procedure was demonstrated in four different genotypes. It is of note that the beneficial effect of pre-culturing anthers on a high sucrose medium was likely due to an osmotic effect rather than a nutritional effect, as pre-culture of anthers on medium containing 6% sucrose and 9% polyethylene glycol (PEG) for 7 days before transfer to the medium only containing 6% sucrose had the same beneficial effect as pre-culture of anthers on medium containing 15% sucrose. Pre-culturing anthers on medium containing sucrose up to 21% for 7 days before transfer to a low sucrose medium also had the same beneficial effect. It is clear that other osmotic regulators, for example, but by no means limited to, maltose, lactose, glucose, mannitol and sorbitol, may have the similar beneficial effect as the high sucrose or PEG in increasing the overall efficiency of plant regeneration and reducing the frequency of regeneration from the somatic tissues of anthers.

Pre-culturing of anthers on a high 2,4-D medium for a period of time before transfer to a low 2,4-D medium resulted in the increase of overall efficiency of regeneration and anther efficiency. Subsequently a high sucrose concentration and a high 2,4-D concentration were incorporated into the experiment to investigate the effect of pre-culturing of anthers on a high salt concentration medium on callus induction and shoot regeneration. As discussed above, the beneficial effect of pre-culturing of anthers on high salt concentration in increasing plant regeneration efficiency is likely attributable to the osmotic effect. The most efficient protocol for doubled haploid production combined the pre-culture of anthers on high osmotic regulator, auxin and mineral salt into a single step and have been used effectively to produce a large number of doubled haploid plants from many crosses with diverse genetic background.

Using the protocols developed for doubled haploid production, we were able to produce fertile transgenic flax at a very high frequency and reduce the escapes to a very low level. Using anther culture-derived calluses as the ex-plants and a two-week selection regime, a transformation efficiency of 66% and an escape frequency of under 27% was achieved. This transformation efficiency was 4.0 times higher than the best reported transformation efficiency using hypocotyls as the ex-plants in Agrobacterium tumefaciens based transformation or particle bombardment based transformation (Dong and McHughen 1993; Wijayanto and McHughen 1999). Since multiple GUS foci were found in GUS staining of callus and multiple shoots regenerated from different areas of the callus were visibly obvious, the actual number of independent transformation events was much greater than the transformation efficiency based on the number of callus producing at least one GUS positive plant. Furthermore, the frequency of escape in anther-culture derived callus based transformation protocol was very low, one third of that in hypocotyl based transformation protocol (over 80%) or half of that in particle bombardment based transformation (54%) (Dong and McHughen 1993; Wijayanto and McHughen 1999). The frequency of escape in anther-culture derived callus-based transformation was calculated based on the number of shooting calluses producing GUS negative shoots/the total number of calluses producing shoots in regeneration medium without subject to further antibiotic selection.

The high transformation efficiency and low frequency of escape obtained in our anther culture-derived callus based transformation system may be due to the fact that these callus cells are amenable to Agrobacterium infection and that infected cells have very high regeneration capacity based on our protocols. The very high efficiency transformation protocols developed in this study would be useful to pyramid genes into the same plants and to conduct many metabolic engineering applications by co-transformation. Furthermore, the increased frequency of transformation makes it possible to segregate out independently integrated selectable markers. The high efficiency transformation system would also be valuable for gene discovery, gene expression and functional genomic studies. In addition, this system could be used to develop site-specific or homologous integration transformation protocols. Examples of suitable transgenes include but are by no means limited to herbicide genes, insect resistance genes, disease resistance genes, metabolic genes, modified starch production genes, modified protein production genes, modified fatty acid production genes, stress tolerance genes, antisense genes that suppress endogenous gene function, genes encoding a product that can be isolated from the plant in a purified form, such as a drug or an antibody, or selectable marker genes. As used herein, "transgene" refers to a nucleic acid sequence introduced into a plant, plant tissue or plant cell by transformation.

In another embodiment of the invention, the anther culture callus-based transformation method is used to develop a high throughput transformation system. As will be apparent to one skilled in the art, for metabolic engineering and other applications using cotransformation of multiple genes or multiple constructs, the number of transgenic plants required is large, and is even larger in applications involving gene discovery and functional genomics. The fact that flax has the smallest genome size of the major field crops combined with the high throughput transformation protocol described herein indicates that flax may join Aradopsis, tobacco and Micro Tom tomato as a model species for gene discovery and functional genomics.

While the preferred embodiments of the invention have been described above, it will be recognized and understood that various modifications may be made therein, and the appended claims are intended to cover all such modifications which may fall within the spirit and scope of the invention.

TABLE 1

The effect of pre-culture of anthers on a high sucrose medium on callus induction and shoot regeneration

| Genotype | Treatment (days) | Percentage of anthers producing calluses (%) | Overall efficiency of regeneration (%) | Anther efficiency (%) |
|---|---|---|---|---|
| 98-200 | CK | 57.3 b | 61.9 b | 34.2 b |
| | 2 d | 68.5 ab | 105.0 a | 49.2 a |
| | 7 d | 80.0 a | 116.9 a | 56.2 a |
| | 14 d | 75.4 a | 66.5 b | 49.2 a |
| | 28 d | 65.8 b | 32.7 c | 27.7 b |
| A proprietary line | CK | 25.8 a | 32.8 b | 16.5 a |
| | 2 d | 34.8 a | 50.8 a | 20.3 a |
| | 7 d | 29.3 a | 38.3 ab | 19.5 a |
| | 14 d | 14.8 b | 3.3 c | 3.0 b |
| | 28 d | 24.0 a | 3.0 c | 2.5 b |
| 96-45 | CK | 45.0 b | 18.0 b | 11.8 cd |
| | 2 d | 64.5 a | 31.3 a | 22.0 ab |
| | 7 d | 56.8 a | 36.8 a | 25.0 a |
| | 14 d | 48.3 b | 21.3 b | 16.3 abc |
| | 28 d | 28.3 c | 5.8 c | 5.0 cd |
| 96-3 | CK | 20.6 c | 14.1 cd | 6.7 b |
| | 2 d | 57.6 a | 35.6 a | 21.2 a |
| | 7 d | 43.2 b | 29.4 ab | 17.6 a |
| | 14 d | 43.2 b | 21.2 bc | 16.4 a |
| | 28 d | 13.8 c | 4.4 d | 4.4 b |

TABLE 2

The effect of pre-culture of anthers on a high sucrose medium on the percentage of microspore-derived plants

| Treatment | Percentage of microspore-derived plants |
|---|---|
| CK | 47.9 |
| 2 d | 79.1 |
| 7 d | 92.4 |
| 14 d | 92.2 |
| 28 d | 89.1 |

TABLE 3

The effect of PEG on callus induction and shoot regeneration

| Treatment | Percentage of anthers producing calluses (%) | Overall efficiency of regeneration (%) | Anther efficiency (%) |
|---|---|---|---|
| $A_{22}C$-15 | 73.9 b | 77.8 a | 36.1 a |
| PEG-9 | 70.6 b | 68.9 a | 33.9 a |
| PEG-12 | 88.3 a | 57.8 a | 28.3 a |
| PEG-15 | 12.2 c | 14.4 b | 6.1 b |

TABLE 4

Effect of salt concentration at the second step of induction on callus induction and shoot regeneration

| Genotype | Treatment | Percentage of anthers producing calluses (%) | Overall efficiency of regeneration (%) | Anther efficiency (%) |
|---|---|---|---|---|
| 99-182 | A22C | 52.6 | 15.8 | 11.4 |
|  | ¼ A22C | 58.6 n.s. | 20.5 n.s | 15.8 n.s. |
| 99-183 | A22C | 63.2 | 12.7 | 10.2 |
|  | ¼ A22C | 63.9 n.s. | 20.6 * | 15.6 * |
| 98-87 | A22C | 36.3 | 16.1 | 10.4 |
|  | ¼ A22C | 37.5 n.s. | 33.6 * | 18.1 * |
| 98-88 | A22C | 24.7 | 4.2 | 3.3 |
|  | ¼ A22C | 23.2 n.s. | 8.9 * | 6.3 * |

TABLE 5

The effect of sucrose concentration during pre-culture on callus induction and shoot regeneration

| Sucrose concentration (g/L) | Percentage of anthers producing calluses (%) | Overall efficiency of regeneration (%) | Anther efficiency (%) |
|---|---|---|---|
| 150 | 53.0 b | 82.3 b | 38.0 b |
| 180 | 68.7 a | 124.0 a | 57.0 a |
| 210 | 40.7 b | 63.7 b | 32.7 b |
| 240 | 18.0 c | 21.7 c | 12.7 c |

TABLE 6

The effect of sucrose concentration at the second step of callus induction on callus induction and shoot regeneration

| Sucrose concentration (g/L) | Percentage of anthers producing calluses (%) | Overall efficiency of regeneration (%) | Anther efficiency (%) |
|---|---|---|---|
| 60 | 76.5 a | 75.9 a | 45.0 a |
| 30 | 68.5 a | 100.6 a | 47.1 a |
| 10 | 65.8 a | 97.1 a | 49.4 a |
| 0 | 31.8 b | 16.8 b | 16.2 b |

TABLE 7

The effect of callus induction selection duration on shoot regeneration and transformation

| Selection regime | Shoot regeneration efficiency (%) | Transformation efficiency (%) | Escape frequency (%) |
|---|---|---|---|
| Two week selection | 89.8 (79/88) | 65.9 (58/88) | 26.6 (21/79) |
| Four week selection | 27.3 (24/88) | 18.2 (16/88) | 33.3 (8/24) |

TABLE 8

The effect of *Agrobacterium* concentration on shoot regeneration and transformation

| *Agrobacterium* concentration | Shoot regeneration efficiency (%) | Transformation efficiency (%) | Escape frequency (%) |
|---|---|---|---|
| OD 0.3 | 67.0 (73/109) | 49.5 (54/109) | 26.3 (19/73) |
| OD 1.2 | 35.0 (35/100) | 29.0 (29/100) | 17.1 (6/35) |

TABLE 9

The effect of the age of ex-plant on shoot regeneration and transformation

| Age of ex-plant | Shoot regeneration efficiency (%) | Transformation efficiency (%) | Escape frequency (%) |
|---|---|---|---|
| Five-week old | 53.3 (32/60) | 43.3 (26/60) | 18.8 (6/32) |
| Seven-week old | 21.7 (13/60) | 21.7 (13/60) | 0 |

TABLE 10

Inheritance of GUS gene in putative transformants derived from co-cultivation of anther-derived calluses with *Agrobacterium*

| Code No. | Positive GUS:Negative GUS | Expected ratio | integrations |
|---|---|---|---|
| TM1 | 31:9 | 3:1 | one |
| TM2 | 67:0 | homozygous |  |
| TM3 | 54:24 | 3:1 | one |
| TM4 | 38:2 | 15:1 | two |
| TM5 | 38:2 | 15:1 | two |
| TM6 | 29:9 | 3:1 | one |
| TM7 | 81:31 | 3:1 | one |
| TM8 | 69:31 | 3:1 | one |
| TM9 | 101:0 | homozygous |  |
| TM10 | 28:12 | 3:1 | one |
| TM11 | 48:25 | 3:1 | one |
| TM12 | 55:10 | 3:1 | one |
| TM13 | 39:13 | 3:1 | one |
| TM14 | 57:18 | 3:1 | one |
| TM15 | 27:5 | 3:1 | one |
| TM16 | 44:42 | chimera |  |
| TM17 | 34:6 | 3:1 | one |
| TM18 | 42:5 | 15:1 | two |
| TM19 | 61:11 | 3:1 | one |
| TM20 | 19:8 | 3:1 | one |

TABLE 10-continued

Inheritance of GUS gene in putative transformants derived from co-cultivation of anther-derived calluses with *Agrobacterium*

| Code No. | Positive GUS:Negative GUS | Expected ratio | integrations |
|---|---|---|---|
| TM21 | 69:25 | 3:1 | one |
| TM22 | 83:35 | 3:1 | one |
| TM23 | 40:33 | chimera | |
| TM24 | 49:15 | 3:1 | one |

The invention claimed is:

1. A method of transforming and regenerating Flax plants comprising:

growing a Flax anther culture-obtained callus on a high osmotic medium selected from the group consisting of 15-24% sucrose, 18-24% sucrose, 15-24% maltose, 6-9% sucrose+6-9% PEG, and 2×-4×$A_{22}$-C salts for 2-14 days;

transferring the anther culture-obtained callus to a low osmotic medium selected from the group consisting of ½-¼ $A_{22}$-C salts and 1-6% sucrose;

transforming the anther culture-obtained callus with a nucleic acid molecule by cocultivating the anther culture-obtained callus with *Agrobacterium*;

growing the callus on a regeneration medium, said regeneration medium for regenerating shoots;

growing the callus on an elongation medium for elongating the shoots;

and transferring the shoots to a rooting medium for growing the Flax plant.

2. The method according to claim 1 wherein the [ callus is transformed by cutting the callus while in an *Agrobacterium* suspension ] transforming step comprises cutting the callus and cocultivating the callus with *Agrobacterium*, and whereby the *Agrobacterium* is in suspension.

3. The method according to claim 1 wherein prior to transformation the callus is 2-7 weeks old.

* * * * *

UNITED STATES PATENT AND TRADEMARK OFFICE
CERTIFICATE OF CORRECTION

PATENT NO.          : 7,297,838 B2                                          Page 1 of 1
APPLICATION NO. : 10/291504
DATED                  : November 20, 2007
INVENTOR(S)        : Yurong Chen and Joseph Clifford Paul Dribnenki It is certified that error appears in the above-identified patent and that said Letters Patent is hereby corrected as shown below:

Title page item (73), "Assignee" - should read

--Agricore United--

Signed and Sealed this

Fifteenth Day of April, 2008

JON W. DUDAS
*Director of the United States Patent and Trademark Office*